US00PP12842P2

(12) United States Plant Patent
Black

(10) Patent No.: US PP12,842 P2
(45) Date of Patent: Aug. 13, 2002

(54) 'HARRY BLACK GALA CULTIVAR'

(75) Inventor: Robert Eugene Black, Thurmont, MD (US)

(73) Assignee: International Plant Management, Inc., Lawrence, MI (US)

( * ) Notice: Subject to any disclaimer, the term of this patent is extended or adjusted under 35 U.S.C. 154(b) by 0 days.

(21) Appl. No.: 09/571,487

(22) Filed: May 15, 2000

(51) Int. Cl.[7] ..... A01H 5/00
(52) U.S. Cl. ..... Plt./162
(58) Field of Search ..... Plt./162

(56) References Cited

U.S. PATENT DOCUMENTS

PP3,637 P * 10/1974 McKenzie
PP4,121 P * 10/1977 Tenttove
PP6,172 P * 5/1988 Creech
PP6,955 P * 8/1989 Kiddle
PP7,396 P * 12/1990 Cooper
PP7,589 P * 7/1991 Fulford et al.
PP8,621 P * 3/1994 Olsen et al.
PP8,673 P * 4/1994 Waliser
PP8,720 P * 5/1994 Hill
PP9,681 P * 11/1996 Olsen et al.
PP10,016 P * 9/1997 Brookfield et al.
PP10,114 P * 11/1997 Gale
PP10,458 P * 6/1998 Fackler
PP10,840 P * 3/1999 Simmons et al.

* cited by examiner

*Primary Examiner*—Bruce R. Campell
*Assistant Examiner*—Susan B. McCormick

(57) ABSTRACT

A new and distinct variety of Gala apple tree originating as a limb mutation of the *Malus sylvestris* variety of Gala, 'McKenzie' cultivar (U.S. Plant Pat. No. 3,637). This new variety is unique from its parent and other Gala cultivars because the fruit ripens 5 weeks later than the parent and Gala cultivars. The new variety is firmer than other Gala cultivars, averaging 18 to 23 pounds pressure at maturity.

3 Drawing Sheets

FIELD OF THE INVENTION

A new and distinct variety of apple tree originating as a limb mutation of the *Malus sylvestris* variety of Kidds D-8 Gala, 'McKenzie' cultivar, U.S. Plant Pat. No. 3,637, hereinafter referred to as the 'Harry Black Gala'. Class: PLT. This new sport is unique from its parent because the fruit ripens 5 weeks later than its parent and is substantially firmer than the parent.

DESCRIPTION OF PRIOR ART

The new variety, 'Harry Black Gala', differs from its parent and other Gala varieties in the following characteristics:

A. The new variety ripens 5 weeks later than its parent, 'McKenzie' (U.S. Plant Pat. No. 3,637) and the following Gala cultivars: 'Royal Gala' (U.S. Plant Pat. No. 4,121), 'Scarlet Gala' (U.S. Plant Pat. No. 6,172), 'Galaxy' (U.S. Plant Pat. No. 6,955), 'Treco Spur Gala No. 42' (U.S. Plant Pat. No. 7,396), 'Fulford' (U.S. Plant Pat. No. 7,589), 'Obragala' (U.S. Plant Pat. No. 8,621), 'Waliser' (U.S. Plant Pat. No. 8,673), 'Applewaites' (U.S. Plant Pat. No. 8,720), 'Baigent' (U.S. Plant Pat. No. 10,016), 'Gale' (U.S. Plant Pat. No. 10,114), 'Big Red Gala' (U.S. Plant Pat. No. 10,458), and 'Simmons' (U.S. Plant Pat. No. 10,840). The new variety ripens 6 weeks later than 'Olsentwo Gala' (U.S. Plant Pat. No. 9,681).

B. The fruit of the new variety is firmer than its parent at commercial maturity. The new variety pressure tests at 18 to 23 pounds at commercial maturity while its parent averages 15 to 17 pounds at commercial maturity.

SUMMARY OF THE INVENTION

This new and distinct variety of Gala apple tree was discovered in 1993 as a limb mutation of 'McKenzie' cultivar, U.S. Plant Pat. No. 3,637, in an orchard planted in 1984 in Thurmont, Md. The new variety was noticed because the fruit ripens 5 weeks later than the parent and is much firmer than the parent. Observations during the next several seasons confirmed the late ripening and firmness. In October of 1994, buds were taken from the original tree and trees for further testing were asexually produced on M9-337 and EMLA 26 rootstocks and remains true to the description herein contained. It has not been reproduced on its own root.

A BRIEF DESCRIPTION OF THE DRAWINGS

The accompanying photographs show typical specimens of the new variety as depicted in color as nearly true as is reasonably possible in color illustrations of this character. These specimens were obtained in Van Buren County, Mich.

FIG. 1 illustrates the fruits of the new variety at maturity.

FIG. 2 illustrates the leaves of the new variety.

FIG. 3 illustrates a bloom of the new variety.

A BOTANICAL DESCRIPTION OF THE PLANT

A detailed description of the 'Harry Black Gala' cultivar follows using The Royal Horticultural Society of London Colour Chart for color identification.

Parentage: Limb mutation of 'McKenzie' cultivar, (U.S. Plant Pat. No. 3,637).

Location of observations: Thurmont, Frederick County, Md.

Tree:

*Age of specimen.*—8 years.

*Size.*—Height: 3.5 m, width: 3 m.

*Vigor.*—Vigorous, averaging 40 to 60 mm in growth per year.

*Density.*—Open, 10 major scaffolds in 3 layers on the specimen tree.

*Form.*—Rounded, spreading.

*Production.*—Approximately 42 pounds per bushel with an average production of 800 bushels per acre on a dwarfing rootstock such as M26 or M9.

*Growth type.*—Upright with a slight weeping habit.

*Bearing.*—Annual.

Trunk:

*Diameter of trunk 150 mm above bud union.*—70 mm.

*Trunk bark color.*—Grayed Green 199A.

*Surface.*—Smooth.

*Lenticel size 15 mm above ground.*—Length: 3 to 5 mm, width: 0.5 mm.

*Number of lenticles per cm*$^2$.—1.

*Lenticel color.*—Gray 201 B.

Branches:

*Surface.*—Smooth.

*Color.*—Brown 200 B.

*Form.*—Profuse branching.

*Average diameter,* 1 year old branch.—5 mm.

*Average diameter,* 2 year old branch.—12 mm.

*Average diameter,* 3 year old branch.—25 mm.

*Average crotch angle.*—60°.

*Buds position.*—Alternate, situated tightly applied to the branch.

*Branch lenticels.*—Prominent, numerous.

*Branch lenticel length.*—1–2 mm.

*Branch lenticel width.*—0.5 mm.

*Branch lenticel color.*—Grayed white 156C.

Leaves:

*Size.*—Length 85 mm, width 45 mm.

*Texture.*—Leathery, crisp.

*Form.*—Ovate.

*Base.*—Rounded.

*Apex.*—Acute.

*Venation.*—Pinnate, 10–12 veins, mainly alternate.

*Mid-vein.*—Mainly Yellow Green 147 B.

*Margin.*—Crenate.

*Petiole length.*—25 mm.

*Petiole width.*—2 mm.

*Petiole color.*—Yellow Green 146 E with some Red 53 A.

*Stipules.*—Very fine, at the base of the petiole on almost all leaves.

*Stipule length.*—7 mm.

*Stipule width.*—0.5 mm.

*Stipule color.*—Yellow Green 147 B.

*Adaxial surface pubescence.*—None.

*Abaxial pubescence.*—Very fine.

*Adaxial surface color.*—Yellow Green 147 A.

*Abaxial surface color.*—Yellow Green 147 B.

Leaf buds: Observations taken at full dormancy.

*Length.*—4 mm.

*Width.*—2 mm.

*Color.*—Black 202 B.

*Placement on branch.*—Tightly applied to the branch.

*Internode distance.*—20 mm.

Flower buds at popcorn stage:

*Stalk length.*—37 mm.

*Stalk color.*—Yellow Green 144 A.

*Bud.*—Length 10 mm, width 8 mm.

*Bud color.*—Red 46 A veination and blush with background of White 155 D.

Flowers:

*Bloom timing.*—Midseason bloom with a long bloom period, 4 to 5 days after parent.

*Bloom period.*—May 1st to 7$^{th}$ Thurmont, Md.

*Number of flowers per cluster.*—5 to 6.

*Fragrance.*—Faint.

*Bloom diameter.*—60 mm.

*Bloom depth (from pedicel to anther).*—12 mm.

*Stamens.*—Numerous, white, anthers Yellow 12A.

*Sepal number.*—5.

*Sepal length.*—8 mm.

*Sepal width.*—4 mm.

*Sepal color.*—Yellow green 144 A.

*Petal length.*—26 mm.

*Petal width.*—14 mm.

*Petal shape.*—Ovate.

*Petal margin.*—Even with some ruffling at the apex.

*Petal apex.*—Rounded.

*Petal base.*—Rounded to acuminate at junction with receptacle.

*Petal color.*—Adaxile: White 155 D with faint veination of Red 46 A. Abaxile: White 155 D with prominent veination of Red 46 A.

*Petal texture.*—Soft.

Fruit:

*Maturity when described.*—Firm ripe, 19 pounds pressure.

*Date of picking.*—October 5 to 10 in Thurmont, Fredrick County, Md.

*Size.*—Axial diameter 62 to 65 mm., transverse diameter 75 to 80 mm.

*Form.*—Uniform, symmetrical, regular, globose.

*Cavity.*—Symmetrical, abrupt at base, depth, 15 mm; breadth, 22 mm.

*Basin.*—Symmetrical, abrupt at base, wide, depth, 8 mm, width 19 mm.

*Calyx segments.*—Persistent, erect, outer and inner surfaces pubescent.

*Eye.*—Closed.

*Stem.*—36 mm in length with 50% of total length extending above the shoulders.

Skin:

*Thickness.*—Medium thick.

*Texture.*—Very smooth, glossy with medium cuticle wax.

*Tendency to crack.*—None.

*Lenticels.*—Yellow Orange 21 C, prominent, large, numerous.

*Color.*—Solid blush of Red Group 53 A over Yellow Orange 21 C background.

Flesh:

*Texture.*—Crisp.

*Aroma.*—Sweet, aromatic.

*Color.*—Yellow Orange 15 B.

*Texture.*—Firm, tender, fine crisp.

*Eating quality.*—Tart, juicy, excellent flavor.

Core:

*Bundle area.*—Small, oblate, symmetrical at base.

*Bundle.*—Inconspicuous, Yellow Orange 15 A.

*Capillary area*.—Distinct.
*Calyx tube*.—Funnel form.
*Depth of tube to shoulder*.—16 mm.
*Axillary cavity*.—Present.
*Seed cells*.—Axile, walls thin, tough, length 16 mm, breadth 7 mm.
*Longitudinal section*.—Broadly ovate.

Seeds: Number perfect, 6 to 10.
*Number in one cell*.—1 to 2.
*Length*.—6 mm.
*Breadth*.—3 mm.
*Form*.—Obtuse, non-tufted.
*Color*.—Brown 200 B.

Use: Processing, fresh market, dessert.

Shipping quality: Excellent.

Keeping quality: Excellent, 90 to 120 days in common storage, 6 months in controlled atmosphere storage.

Tree winter hardiness: Average for an apple variety. Tree is hardy to −20° to −30° F.

Bud winter hardiness: −15° to −20° F., depending on the stage of development of the bud.

Dought tolerance: Average for an apple variety. Normal requirements average ½" of rain per week. Severe drought adversely affects fruit size and quality.

Disease resistance: Very susceptible to fire blight (*Erwinia amylovora*) and other bacterial diseases. Moderately susceptible to apple scab (*Venturia inaequalis*), powdery mildew (*Podosphaera leucotricha*), and other fungal diseases.

I claim:

1. A new and distinct variety of apple tree, *Malus sylvestris*, substantially as herein shown and described, characterized particularly as to novelty by the unique combination of a medium sized, vigorous, rounded tree with fruits that ripen 5 weeks later than other Gala cultivars and with substantially firmer fruits.

* * * * *

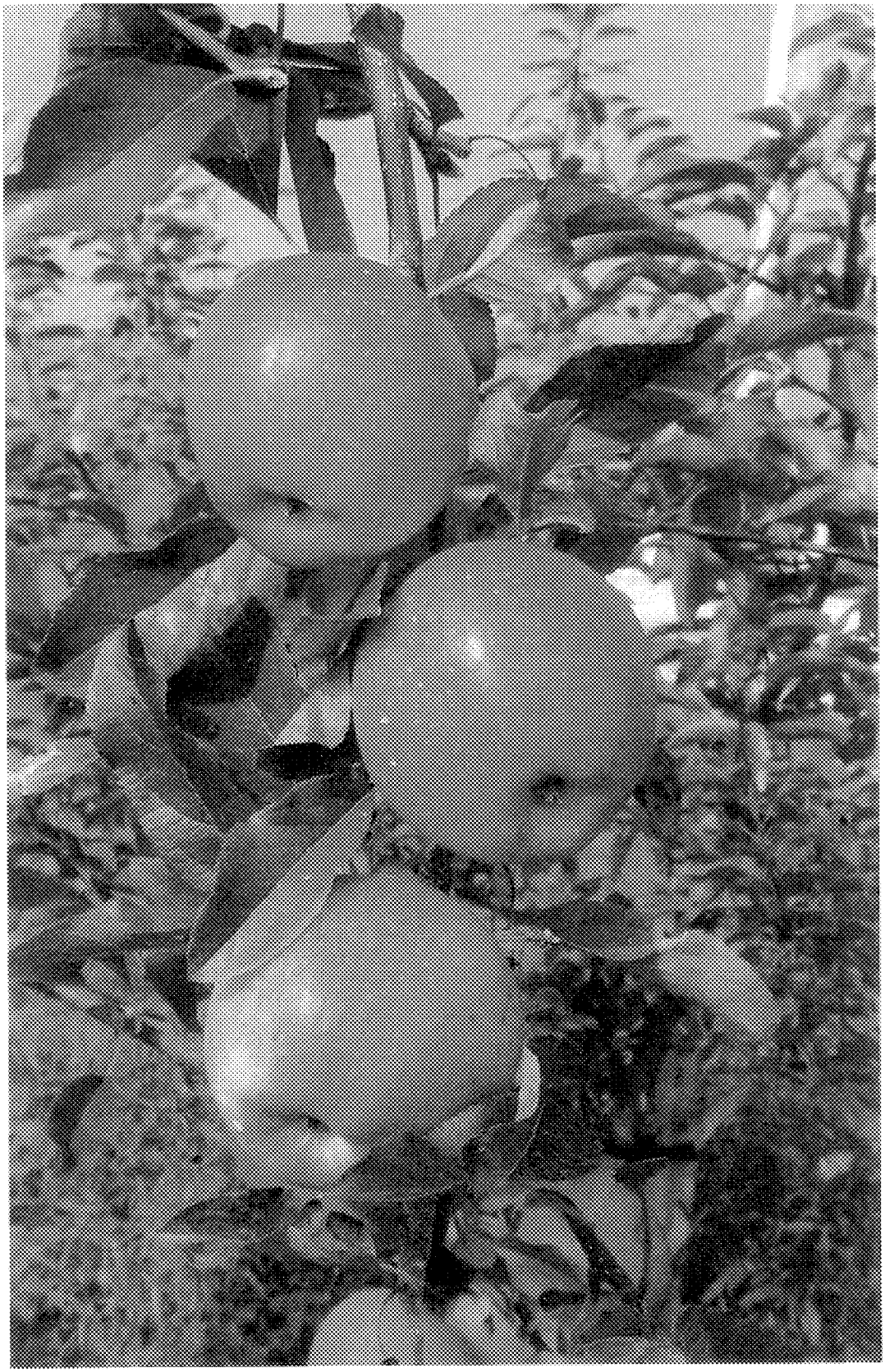

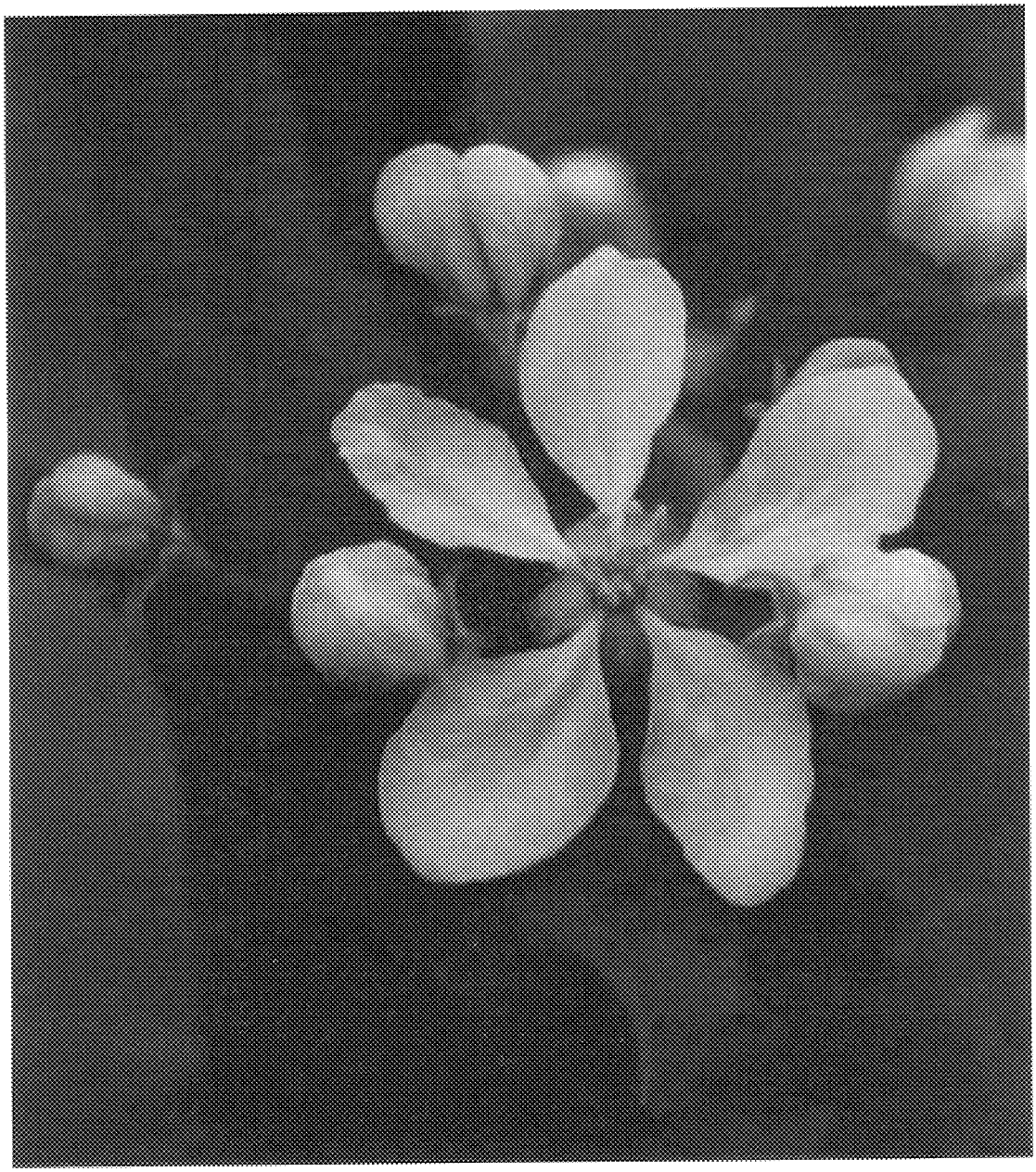

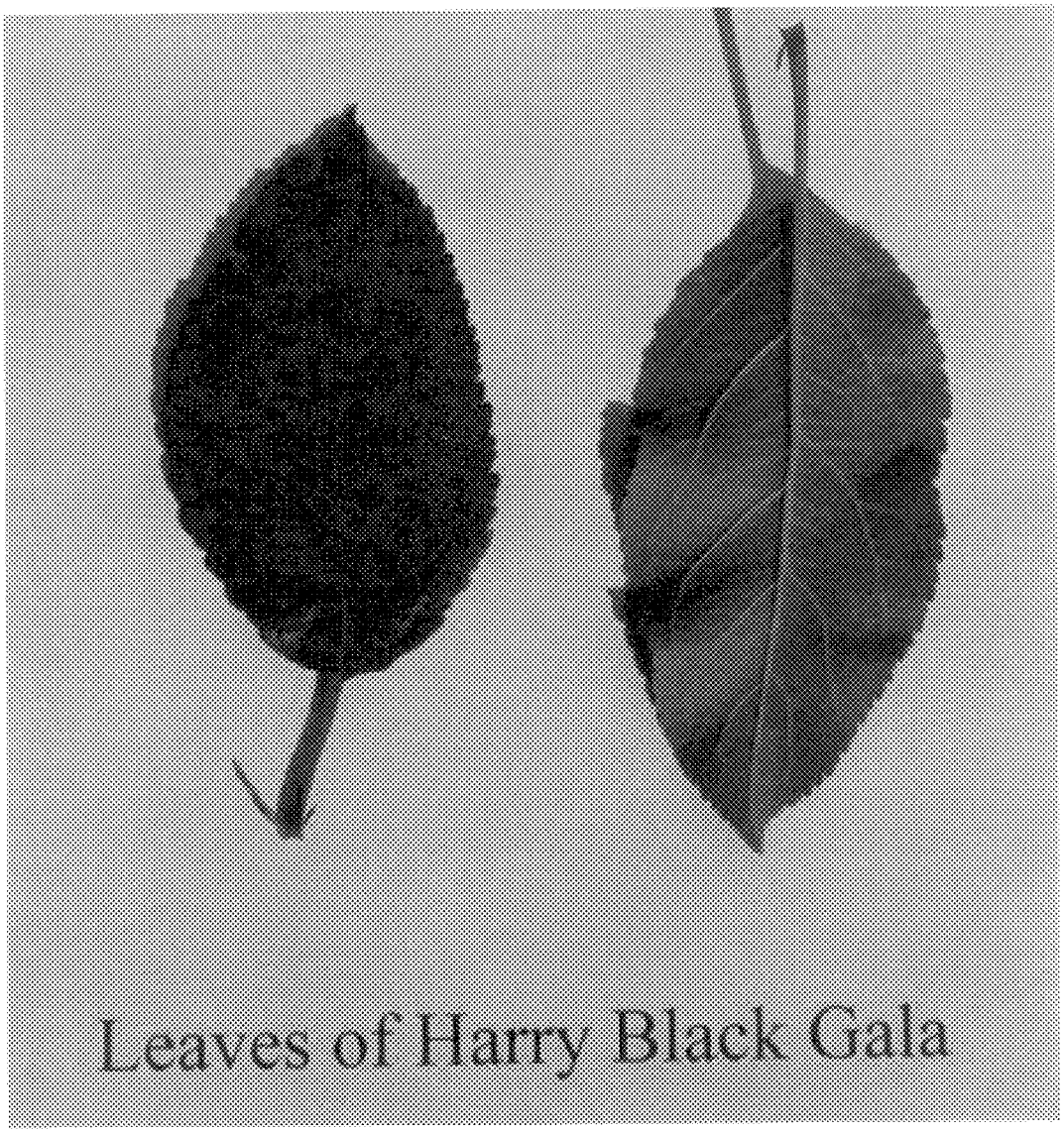
Leaves of Harry Black Gala